US006604004B1

(12) United States Patent
Zelickson et al.

(10) Patent No.: US 6,604,004 B1
(45) Date of Patent: Aug. 5, 2003

(54) DEVICE AND METHOD FOR TREATMENT OF GASTROESOPHAGEAL REFLUX DISEASE

(76) Inventors: Brian D. Zelickson, 2764 Drew Ave. South, Minneapolis, MN (US) 55416; Robert A. Ganz, 1431 Lakeview, Minneapolis, MN (US) 55416

( * ) Notice: Subject to any disclaimer, the term of this patent is extended or adjusted under 35 U.S.C. 154(b) by 15 days.

(21) Appl. No.: 09/971,315

(22) Filed: Oct. 4, 2001

Related U.S. Application Data

(63) Continuation of application No. 09/475,580, filed on Dec. 30, 1999, now Pat. No. 6,321,121, which is a continuation of application No. 08/749,723, filed on Nov. 15, 1996, now Pat. No. 6,073,052.

(51) Int. Cl.$^7$ ................................................ A61B 18/18

(52) U.S. Cl. ..................... 607/101; 607/99; 607/102; 607/105; 606/28

(58) Field of Search ................... 606/27, 28, 32–33, 606/41, 42, 46, 47; 607/96, 98, 99, 101, 102, 104, 105, 113

(56) References Cited

U.S. PATENT DOCUMENTS

| 4,326,529 A | | 4/1982 | Doss et al. |
| 4,381,007 A | | 4/1983 | Doss |
| 4,646,737 A | * | 3/1987 | Hussein et al. ............... 606/28 |
| 4,662,383 A | * | 5/1987 | Sogawa et al. ............. 607/133 |
| 4,709,698 A | | 12/1987 | Johnston et al. |

(List continued on next page.)

FOREIGN PATENT DOCUMENTS

| EP | 0 422 112 B1 | 7/1996 |

OTHER PUBLICATIONS

R.C.M. McGouran, MD and J.M. Galloway, MD, "A laser–induced scar at the cardia increases the yield pressure of the lower esophageal sphincter," *Gastrointestinal Endoscopy*, vol. 36, Nov. 5, 1990, pp. 439–443.

Hayashi, et al., "The Effect of Non–Ablative Laser Energy on Joint Capsular Properties: An In Vitro Mechanical Study using a Rabbit Model," *Comparative Orthopaedic Research Laboratory, University of Wisconsin–Madison*, Mar. 1994, pp. 1–22.

Hayashi, et al., "The Effect of Non–Ablative Laser Energy on the Ultrastructure of Joint Capsular Collagen," *Comparative Orthopaedic Research Laboratory, University of Wisconsin–Madison*, Jan. 1995, pp. 1–22.

Zhou, et al., Thermal Modeling of Laser Photo Thermo Keratoplasty (LPTK), *Opthalmic Technologies II*, SPIE vol. 1644, 1992, pp. 61–133.

Fitzpatrick, et al., "Pulsed Carbon Dioxide Laser Resurfacing of Photoaged Facial Skin," *Arch Dermatol*, Apr. 1996, vol. 132, pp. 395–401.

Hruza, et al., "Laser Skin Resurfacing," *Arch Dermatol*, Apr. 1996, vol. 132, pp 451–455.

*Primary Examiner*—Roy D. Gibson
(74) *Attorney, Agent, or Firm*—Fredrikson & Byron, P.A.

(57) ABSTRACT

A lower esophageal sphincter tightening device for treating gastroesophageal reflux disease which includes an insertion device, an energy source, and an energy transmitting device. The insertion device, by insertion through a body opening, positions the energy transmitting device in the proximity of the lower esophageal sphincter. The energy source generates and transmits energy via the insertion device to the energy transmitting device which directs the transmitted energy onto the lower esophageal sphincter which is comprised largely of collagen. The energy sources transmits energy at a level sufficient to cause heating of the sphincter's collagen resulting in a shrinkage of the collagen and a tightening of the sphincter.

12 Claims, 3 Drawing Sheets

U.S. PATENT DOCUMENTS

| | | | |
|---|---|---|---|
| 5,103,804 A | * | 4/1992 | Abele et al. ............... 600/116 |
| 5,220,927 A | | 6/1993 | Astrahan et al. |
| 5,304,169 A | | 4/1994 | Sand |
| 5,348,551 A | | 9/1994 | Spears et al. |
| 5,364,390 A | | 11/1994 | Taboada et al. |
| 5,374,265 A | | 12/1994 | Sand |
| 5,437,658 A | | 8/1995 | Muller et al. |
| 5,458,596 A | | 10/1995 | Lax et al. |
| 5,484,432 A | | 1/1996 | Sand |
| 5,505,730 A | | 4/1996 | Edwards |
| 5,509,929 A | | 4/1996 | Hascoet et al. |
| 5,540,679 A | | 7/1996 | Fram et al. |
| 5,558,672 A | | 9/1996 | Edwards et al. |
| 5,569,241 A | | 10/1996 | Edwards |
| 5,575,788 A | | 11/1996 | Baker et al. |
| 5,620,480 A | | 4/1997 | Rudie |
| 5,658,278 A | | 8/1997 | Imran et al. |
| 5,964,755 A | | 10/1999 | Edwards |
| 6,006,755 A | | 12/1999 | Edwards |

* cited by examiner

DEVICE AND METHOD FOR TREATMENT OF GASTROESOPHAGEAL REFLUX DISEASE

This application is a continuation of Ser. No. 09/475,580 filed Dec. 30, 1999, U.S. Pat. No. 6,321,121 which is a continuation of Ser. No. 08/749,723 filed Nov. 15, 1996, U.S. Pat. No. 6,073,052.

BACKGROUND OF THE INVENTION

The invention pertains to the treatment of gastroesophageal reflux disease (GERD).

GERD is a major health problem in the United States and worldwide. It affects tens of millions of people and costs billions of dollars to treat. GERD is the reflux of gastric contents from a stomach into a lower area of an esophagus. The gastric contents include acid secreted by the stomach which causes discomfort and eventual damage to an inner lining of the esophagus if left untreated.

The gastric contents are normally prevented from entering the esophagus by a lower esophageal sphincter (LES) mechanism. The LES is a physiologic, non-anatomic area involving the lower 3 centimeters of the esophagus and like other smooth muscle sphincters in the body, anal or urinary, it is tonically contracted to prevent reflux. A healthy LES opens for a brief period of several; seconds in response to swallowing to allow the passage of food. It then quickly regains its tone when the food has passed.

GERD occurs when the sphincter mechanism of the LES fails to work properly. Generally, GERD takes one of three forms: (i) complete weakness of the sphincter musculature in response to a hiatal hernia or an intrinsic weakness that occurs commonly resulting in free reflux, which is poorly understood; (ii) partial weakness of the sphincter that allows reflux when stressed such as a Valsalva maneuver, or (iii) transient or sudden inappropriate relaxation of an otherwise normally toned sphincter.

Treatment of a weakened or inappropriately relaxing sphincter can be either medical or surgical. Known medical treatments include measures or medications that attempt to decrease acid secretion, increase gastric emptying or strengthen the LES. However, the medications are expensive and the measures typically have to be continued on a life long basis.

A more permanent treatment method for GERD can be performed surgically. Surgical methods attempt to strengthen the LES by incising the stomach and wrapping a portion of the stomach around the lower section of the esophagus. This technique is known as a fundoplication. However, surgical treatment requires longer post treatment care, increased pain and recovery time, as well as the associated risks with any surgical procedure.

The latest developments for treating GERD have attempted to provide a minimally invasive procedure to strengthen the lower esophageal area One such treatment is disclosed by C. P. Swain et al., *Knot Tying At Flexible Endoscopy*, Gastrointestinal Endoscopy, 1994; 40:722–29, that calls for endoscopic sewing in the lower esophageal area. However the sewn portion of the esophagus in the Swain technique may relax again requiring further or alternate forms of treatment Another technique disclosed by Donahue injects noxious, scarring substances into the lower esophageal area to create a fibrous reaction P. E. Donahue, et. al., *Endoscopic Ultrasonography Verifies Effect On Endoscopic Treatment Of Reflux In Dogs And Man*, Surgical Endoscopy, 1993;7:524–28. However, the Donahue technique may require numerous and repeated injections.

The esophagus and LES are composed of three tissue layers; a mucosa or inner layer, a submucosa or middle layer, and a muscle or an outer layer. The submucosa layer is largely composed of collagen. It is well-known that heating of collagen tissue within an appropriate temperature range results in a tightening or shrinkage of the collagen tissue. However, there exists no known device or technique for strengthening the LES by shrinkage of collagen tissue as a means to treat GERD.

SUMMARY OF THE INVENTION

The invention discloses a device and method to prevent gastroesophageal reflux or GERD. The device comprises an insertion device, an energy source, and an energy transmitting device. The insertion device has a proximal end connected to the energy source and a distal end connected to the energy transmitting device. The energy source generates and transmits energy to the energy transmitting device through the insertion device. The energy transmitting device then radiates and directs the transmitted energy onto a target area. The insertion device positions the energy transmitting device in the proximity of a lower esophageal sphincter, such that the sphincter tissue becomes the target area of the energy transmitting device.

The energy source then generates and transmits energy to the energy transmitting device which radiates the energy onto the sphincter tissue. The sphincter tissue absorbs the radiated energy which generates heat within the sphincter tissue. The sphincter tissue is largely comprised of collagen which exhibits shrinkage when heated.

The energy source generates and transmits energy at a level sufficient to cause heating of the sphincter tissue to a temperature of between 50° C. and 70° C. (preferably between 63° C. and 65° C. within a time period of between about 1 microsecond and 1 minute. Heating the sphincter tissue within the appropriate range achieves sufficient collagen shrinkage to tighten the lower esophageal sphincter and prevent reflux.

DETAILED DESCRIPTION OF THE PREFERRED EMBODIMENTS

Figure 1:
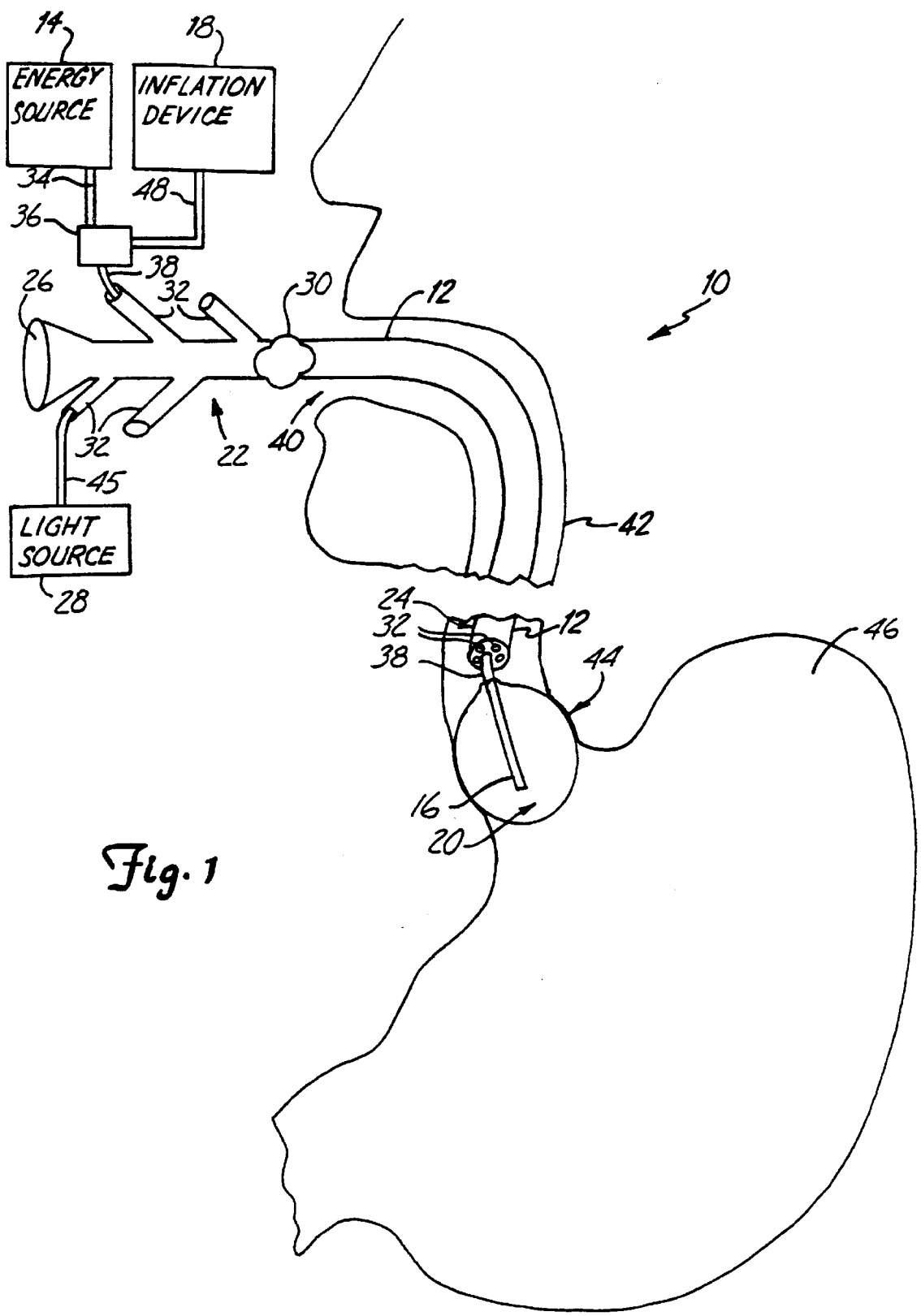
FIG. 1 is a perspective view of a lower esophageal sphincter tightening device of the present invention.

FIG. 1, a preferred embodiment of a lower esophageal sphincter (LES) tightening device 10 is shown in use. The LES tightening device 10 comprises an insertion device 12, an energy source 14 and an energy transmitting device 16. As shown in FIG. 1, the LES tightening device 10 could also include an inflation device 18 and a balloon 20.

Figure 3:
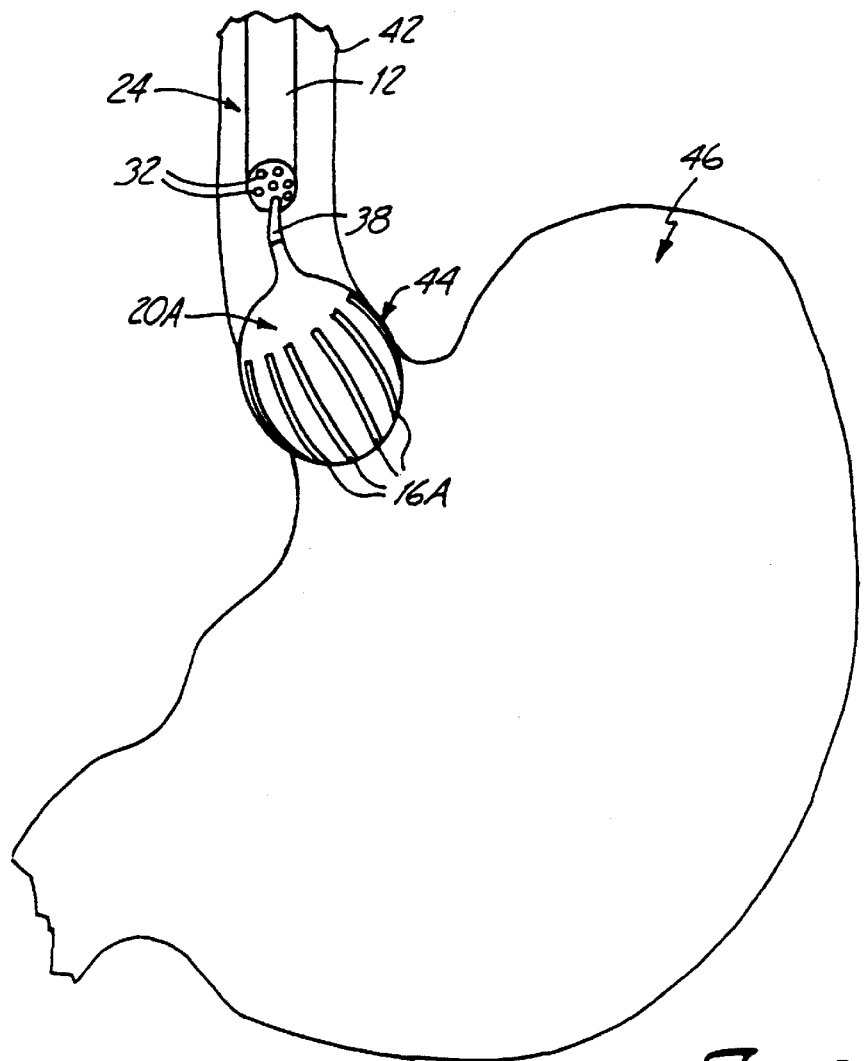
FIG. 3 is a perspective view of a second embodiment of the lower esophageal sphincter tightening device of the present invention.
Figure 4:
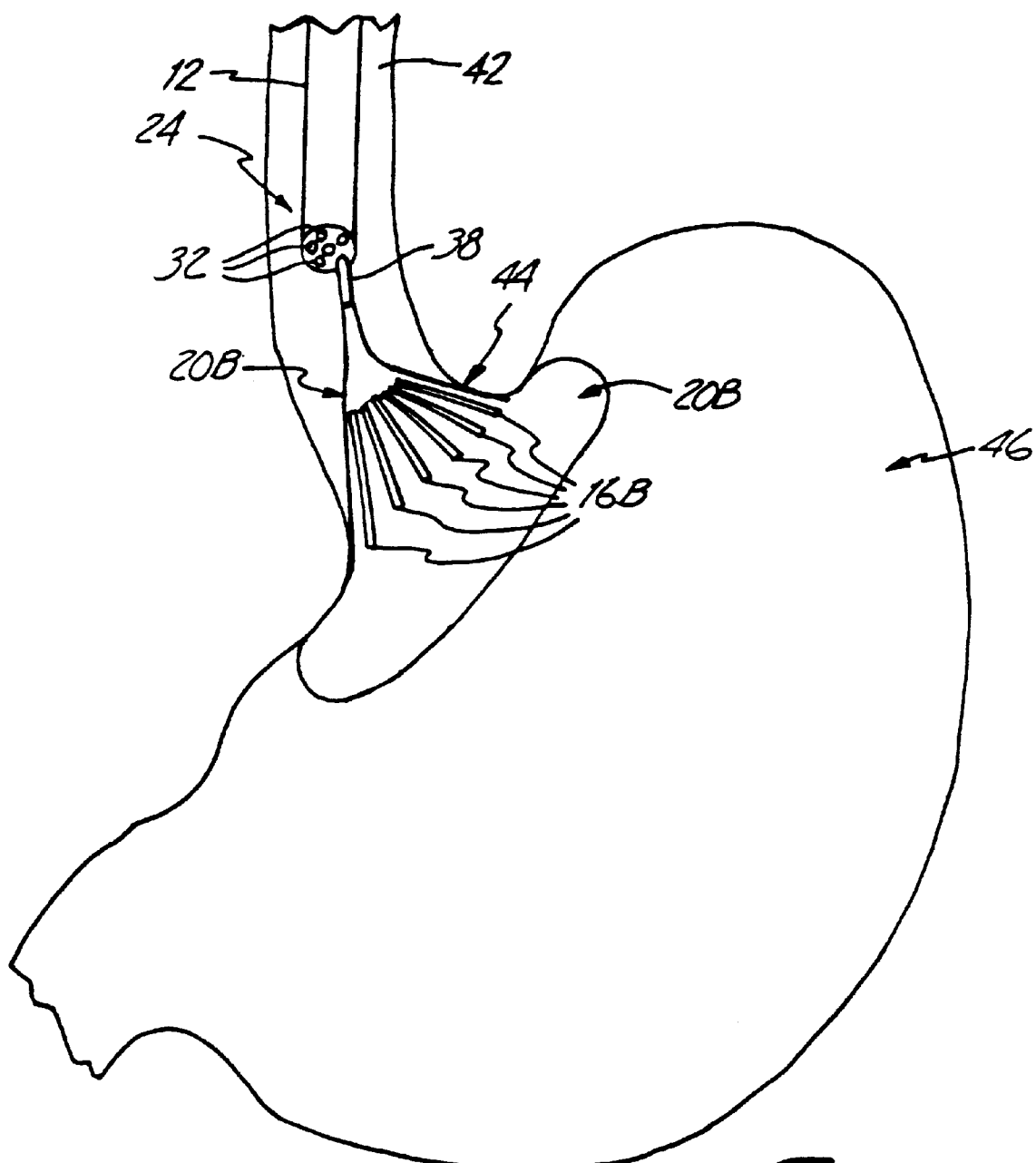
FIG. 4 is a perspective view of a third embodiment of the lower esophageal sphincter tightening device of the present invention.

In a preferred embodiment, the insertion device 12 is an endoscope as shown in FIGS. 1, 3 and 4. However, workers skilled in the art will recognize that a catheter or other similar device could also be used. As shown in FIG. 1, the insertion device 12 has a proximal end 22 and a distal end 24. Additionally, the insertion device 12 could include an eye piece 26, a light source 28 and a control means 30. A series of ports 32 provide access from the proximal end 22 to the distal end 24 through lumens located within the interior of the insertion device 12 along its longitudinal access.

The energy source 14 is located at the proximal end 22 of the insertion device 12. The energy source 14 generates and transmits energy to the energy transmitting device 16 located at the distal end 24 of the insertion device 12. The energy source 14 is connected to the energy transmitting device 16 by a transmission line 34 which passes through a manifold 36. Within the manifold 36, the transmission line 34 becomes part of a catheter 38 that is fed through one of the ports 32 at the proximal end 22. The catheter 38 then passes down one of the interior lumens of the insertion device 12 and is connected to the energy transmitting device 16 at the distal end 24.

In a preferred embodiment, the insertion device 12 enters a body opening 40 and passes down an esophagus 42 until the distal end 24 is in the proximity of a lower esophageal sphincter 44. The control means 30 aid in positioning the distal end 24 of the insertion device 12. Observation through eye piece 26 insures proper placement of the distal end 24. Observation is enabled by the light source 28 which illuminates the area surrounding the distal end 24 by light transmitted through an optical cable 45 which passes through one of the ports 32 and down another interior lumen. The optical cable 45 is preferably a fiber optic bundle.

The energy transmitting device 16 radiates and directs energy received through the catheter 38 from the energy source 14 onto a target area. The distal end 24 of the insertion device 12 is therefore located such that the target area of the energy transmitting device 16 is directed at tissue comprising the lower esophageal sphincter 44. Once the energy transmitting device 16 is properly positioned, the energy source 14 can transmit energy it has generated to the energy transmitting device 16 through the catheter 38.

The transmitted energy is then radiated and directed by the energy transmitting device 16 onto the lower esophageal sphincter 44 tissue. The lower esophageal sphincter 44 tissue absorbs the energy resulting in the generation of heat within the tissue due to thermal conduction. The lower esophageal sphincter 44 tissue is comprised largely of collagen which will exhibit shrinkage characteristics over an appropriate time temperature relationship prior to being damaged or destroyed.

The appropriate time period to satisfy the time temperature relationship is dependent upon the temperature of the treated tissue, which in turn is dependent upon the level of energy generated in the energy source 14 and radiated by the energy transmitting device 16. The desired tissue temperature in the target area is between 50° C. and 70° C., with a preferred level between 63° C. and 65° C. This temperature increase can be achieved within a period of time between one microsecond and one minute dependent upon the amount and type of energy generated within the energy source 14. In a preferred embodiment, the energy source 14 generates radiant energy (e.g. RF or microwave electromagnetic energy) which is transmitted by a transmission line 34 (such as a coaxial cable) that is then contained within the catheter 38 and connects to the energy transmitting device 16. The energy transmitting device 16 is preferably an antenna or a directional antenna.

The LES tightening device 10 can additionally include the inflation device 18 and the balloon 20. Once the energy transmitting device 16 is properly positioned, the balloon 20 is located at the distal end 24 of the insertion device 12 and encapsulates the energy transmitting device 16 as shown in FIG. 1. The inflation device 18, located at the proximal end 22, inflates or deflates the balloon 20 via a conduit 48. The conduit 48 connects the inflation device 18 to the balloon 20 by passing through the manifold. 36, wherein the conduit 48 becomes part of the catheter 38. Air, fluid or gel could be used by the inflation device 18 to inflate the balloon 20. The size of the balloon 20 can be adjusted to maintain proper placement of the energy transmitting device 16 in relation to the lower esophageal sphincter 44 tissue and/or control the amount of collagen shrinkage and therefore control the amount of sphincter tightening.

In a preferred embodiment, the balloon 20 can be either a noncompliant balloon or a compliant balloon. The size of a compliant balloon can be controlled by observation through the eye piece 26, injection of a radiopaque fluid such as fluorochrome into the balloon 20 and viewing on a fluoroscope, or monitoring the pressure of the balloon 20.

Figure 2:
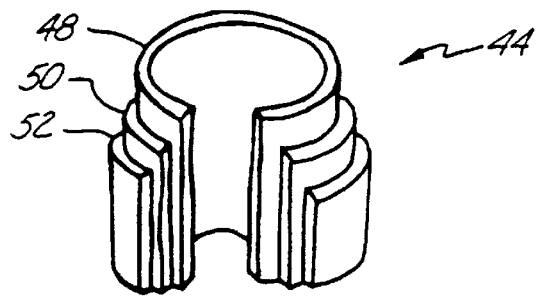
FIG. 2 is a cutaway diagram of an esophagus.

FIG. 2 is a cutaway schematic view (not to scale) of the tissue comprising the lower esophageal sphincter 44. The tissue is comprised of three layers; a mucosa 48 inner layer, a submucosa 50 middle layer and a muscle 52 outer layer. In a preferred embodiment, collagen tissue in the submucosa 50 is targeted for shrinkage. In addition, a cooling means to prevent damage to the mucosa 48 may be incorporated into the LES tightening device 10. This can be accomplished by cooling or cycling through cooled air, liquid, or gel to inflate the balloon 20. The cooled material dissipates the heat generated by absorption of the radiated energy from the energy transmitting device 16. This maintains a safe temperature level in the mucosa 46 (which is less than about 50° C. or preferably less than 45° C.) The type and amount of cooled material used to inflate the balloon 20 is dependent on the amount and type of energy generated within the energy source 14.

FIG. 3 shows a second embodiment of the LES tightening device 10. Reference numerals identical to those employed in connection with FIG. 1 indicate identical elements, and reference numerals followed by a suffix indicate modified but similar elements. In this preferred embodiment, the energy transmitting device 16A is attached to the outer surface of the balloon 20A to direct energy at the lower esophageal sphincter 44 tissue. As previously described, once the distal end 24 of the insertion device 12 properly positions the energy transmitting device 16A over the lower esophageal sphincter 44 tissue, the balloon 20A can be inflated and the energy source 14 can transmit energy to the energy transmitting device 16A for radiation onto the lower esophageal sphincter 44 tissue. Again, a coolant can be used to inflate the balloon 20A to prevent damage to the mucosa 48 while achieving collagen shrinkage in the submucosa 50 resulting in the tightening of the lower esophageal sphincter 44.

A third alternative embodiment to the present invention is depicted in FIG. 4. Again, reference numerals identical to those employed in connection with FIG. 1 indicate identical elements, and reference numerals followed by a suffix indicate modified but similar elements. In this embodiment, the balloon 20B is enlarged to protrude into a stomach 46 and anchor or retain the energy transmitting device 16B in proper position with respect to the lower esophageal sphincter 44 tissue. In this embodiment, the insertion device 12 positions the energy transmitting device 16B such that the target area comprises the lower esophageal sphincter 44 tissue. Once in place, the balloon 20B is enlarged by injection of a suitable material which retains the position of the energy transmitting device 16B relative to the lower esophageal sphincter 44. This assures the energy radiated by the energy transmitting device 16B is absorbed by the lower esophageal sphincter 44. Again, the material injected into the balloon 20B for inflation can be cooled to a sufficient level to offset and dissipate any heat build-up in the mucosa 48 and thereby enable the generation of heat and consequent shrinkage of collagen in the submucosa 50.

Although the present invention has been described with reference to treatment of GERD by toning the muscular LES sphincter, workers skilled in the art will recognize that this device and method could be used to shrink or tone other sphincters located in the body to overcome other medical ailments caused by the loss of sphincter muscle tone. For example, the device and method can be used on the urinary or anal sphincter to overcome incontinence.

Furthermore, workers skilled in the art will also recognize that changes may be made in form and detail without departing from the spirit and scope of the invention. For example, the energy source can generate energy of various wavelengths within the electromagnetic spectrum including but not limited to laser, RF, or microwave energy. Alternatively, the energy source can generate ultrasonic energy to generate heat in the targeted tissue area. The insertion device can be an endoscope, catheter or similar type of device. Depending on the form and wavelength of the energy being used, the energy transmitting device may be an antenna, an ultrasonic transducer, a fiber optic bundle, or an electrical resistance heater. Furthermore, a directional antenna can be used to limit and control the amount of energy directed at specific locations within the targeted tissue.

With the present invention, tissue within the lower esophageal sphincter can be toned or tightened to treat gastroesophageal reflux disease on an outpatient basis with a safe, simple procedure with decreased aftercare, treatment and pain.

What is claimed is:

1. A device for toning or tightening a gastroesophageal sphincter within a body, the device comprising:
   a. an insertion device having a proximal end and a distal end, wherein the insertion device is configured for insertion into a body opening and comprising expandable structure for positioning an energy transmitting device proximate a target area in a tower esophageal sphincter;
   b. an energy source located at the proximal end of the insertion device;
   c. an energy transmitting device located at the distal end of the insertion device; and
   d. observation and control pieces proximate the proximal end to aid in proper positioning of the distal end; and wherein the energy transmitting device is communicably connected to the energy source through the insertion device, and wherein the energy transmitting device comprises a plurality of antennae positioned upon outer or inner surfaces of the expandable structure for directing energy generated by the energy source to an area of tissue making up the targeted tissue area of the sphincter to heat the targeted tissue area to a temperature greater than about 50° C. in the targeted tissue area of the gastroesophageal sphincter.

2. The device of claim 1, further comprising a fiber optic cable at the distal end of the insertion device communicably connected to an eye piece at the proximal end of the device.

3. The device of claim 1, wherein the structure for positioning comprises an expandable structure adapted to prevent dispersion of heat generated in the targeted tissue by compressing the targeted tissue area.

4. The device of claim 1, wherein said energy transmitting device comprises a structure suitable for causing collagen shrinkage for tightening the lower esophageal sphincter.

5. The device of claim 1, wherein the energy transmitting device comprises antennae for directing energy generated by the energy source to an area of tissue making up the targeted tissue area of the sphincter to heat the targeted tissue area to a temperature of between 63° and 65° C. in the targeted tissue area.

6. The device of claim 1, wherein the energy source generates electromagnetic energy.

7. The device of claim 1, wherein the insertion device comprises an endoscope.

8. The device of claim 1, and further including means for cooling surface tissue of the sphincter to prevent surface tissue damage while the energy transmitting device radiates energy.

9. The device of claim 8, wherein the means for cooling dissipates heat generated in the sphincter surface tissue to maintain a temperature below about 50° C. in the surface tissue.

10. The device of claim 1, wherein the expandable structure comprises an inflatable balloon.

11. The device of claim 10, wherein the inflatable balloon is located with the energy transmitting device proximate the distal end of the insertion device and is communicably connected through the insertion device to an inflation device located at the proximal end of the insertion device.

12. The device of claim 1, wherein the energy transmitting device comprises a portion which extends generally radially away from the insertion device.

* * * * *